(12) United States Patent
Vogt

(10) Patent No.: US 9,018,277 B2
(45) Date of Patent: *Apr. 28, 2015

(54) PASTE-LIKE BONE CEMENT

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 72 days.

This patent is subject to a terminal disclaimer.

(21) Appl. No.: 13/715,314

(22) Filed: Dec. 14, 2012

(65) Prior Publication Data

US 2013/0158158 A1   Jun. 20, 2013

(30) Foreign Application Priority Data

Dec. 20, 2011   (EP) .................................. 11009996

(51) Int. Cl.
| | | |
|---|---|---|
| A61L 24/04 | (2006.01) | |
| A61K 6/00 | (2006.01) | |
| A61K 6/083 | (2006.01) | |
| A61L 24/00 | (2006.01) | |
| A61L 27/16 | (2006.01) | |
| A61L 27/26 | (2006.01) | |
| A61L 27/50 | (2006.01) | |
| A61L 24/06 | (2006.01) | |

(52) U.S. Cl.
CPC ............... *A61L 24/043* (2013.01); *A61K 6/005* (2013.01); *A61K 6/083* (2013.01); *A61K 6/0073* (2013.01); *A61L 24/0089* (2013.01); *A61L 27/16* (2013.01); *A61L 27/26* (2013.01); *A61L 27/50* (2013.01); *A61L 24/001* (2013.01); *A61L 24/06* (2013.01); *A61L 2430/02* (2013.01)

(58) Field of Classification Search
CPC ..... A61K 6/005; A61K 6/0073; A61K 6/083; A61L 24/0089; A61L 24/043; A61L 24/06
USPC ........................................................ 523/116
See application file for complete search history.

(56) References Cited

U.S. PATENT DOCUMENTS

| | | | | |
|---|---|---|---|---|
| 3,347,954 A | 10/1967 | Bredereck et al. | | |
| 8,236,871 B2 * | 8/2012 | Hecht et al. | ..................... | 522/24 |
| 8,598,251 B2 * | 12/2013 | Vogt et al. | ..................... | 523/116 |
| 2003/0195273 A1 | 10/2003 | Mitra et al. | | |
| 2007/0233213 A1 * | 10/2007 | Axen et al. | ..................... | 607/113 |
| 2009/0105144 A1 * | 4/2009 | Vogt et al. | ......................... | 514/12 |
| 2009/0105366 A1 | 4/2009 | Vogt et al. | | |
| 2009/0105367 A1 | 4/2009 | Vogt et al. | | |
| 2009/0192239 A1 | 7/2009 | Hecht et al. | | |
| 2011/0112210 A1 | 5/2011 | Vogt et al. | | |
| 2011/0183932 A1 | 7/2011 | Vogt et al. | | |
| 2011/0313078 A1 * | 12/2011 | Vogt et al. | ..................... | 523/116 |

FOREIGN PATENT DOCUMENTS

| | | |
|---|---|---|
| AU | 200054059 B2 | 1/2001 |
| CA | 2742537 A1 | 12/2011 |
| CA | 2783524 A1 | 1/2013 |
| DE | 1495520 A1 | 4/1969 |
| DE | 102007050763 A1 | 4/2009 |
| DE | 102007052116 A1 | 4/2009 |
| DE | 102007050762 B3 | 5/2009 |
| EP | 0674888 A1 | 10/1995 |
| JP | 2003-181270 A | 7/2003 |

OTHER PUBLICATIONS

"Anchorage of the Femoral Head Prosthesis to the Shaft of the Femur", by John Charnley, Manchester, England, The Journal of Bone and Joint Surgery, pp. 28-30, Feb. 1960.
English Language abstract for JP2003-181270 which published on Jul. 2, 2003.
English Language abstract for EP0674888 which published on Oct. 4, 1995.
Canadian Office Action for application CA 2797904 dated Oct. 9, 2013.
Japanese Office Action for application JP 2012-270546 dated Mar. 18, 2014.

* cited by examiner

*Primary Examiner* — Tae H Yoon
(74) *Attorney, Agent, or Firm* — Norris McLaughlin & Marcus, P.A.

(57) ABSTRACT

The present invention relates to a kit comprising at least two pastes, A and B. Paste A contains at least one monomer for radical polymerization; and at least one barbituric acid derivative as polymerization initiator. Paste B contains at least one monomer for radical polymerization; and at least one heavy metal compound as polymerization accelerator that is selected from heavy metal salts and heavy metal complexes. Paste B contains less than 0.01% by weight, relative to the total weight of paste B, of a peroxide; at least one of the pastes A and B contains-at least one filling agent that is poorly soluble or insoluble in the monomer for radical polymerization in either paste A or B respectively; and at least one of the pastes A and B contains at least one inorganic halide salt.

15 Claims, No Drawings

PASTE-LIKE BONE CEMENT

This application claims priority to the European patent application EP11009996.7 filed Dec. 20, 2011.

The present invention relates to a kit and the use of the kit for producing a paste for mechanical fixation of articular endoprostheses, for covering skull defects, for filling bone cavities, for femuroplasty, for vertebroplasty, for kyphoplasty, for the manufacture of spacers or for the production of carrier materials for local antibiotics therapy.

Conventional polymethylmethacrylate bone cements (PMMA bone cements) have been known for decades and are based on the ground-breaking work of Sir Charnley (Charnley, J.: "*Anchorage of the femoral head prosthesis of the shaft of the femur*"; J. Bone Joint Surg. 42 (1960) 28-30). The basic structure of PMMA bone cements has remained the same ever since. PMMA bone cements consist of a liquid monomer component and a powder component. The monomer component generally contains (i) the monomer, methylmethacrylate, and (ii) an activator (e.g. N,N-dimethyl-p-toluidine) dissolved therein. The powder component comprises (i) one or more polymers that are made by polymerisation, preferably by suspension polymerisation, based on methylmethacrylate and co-monomers, such as styrene, methylacrylate or similar monomers, (ii) a radio-opaquer, and (iii) an initiator, (e.g. dibenzoylperoxide). Mixing the powder component and the monomer component, the polymers of the powder component in the methylmethacrylate swell which generates a dough that can be shaped plastically. Simultaneously, the activator, N,N-dimethyl-p-toluidine, reacts with dibenzoylperoxide which disintegrates and forms radicals in the process. The radicals thus formed trigger the radical polymerisation of the methylmethacrylate. Upon advancing polymerisation of the methylmethacrylate, the viscosity of the cement dough increases until the cement dough solidifies and thus is cured.

The essential disadvantage of the previous PMMA bone cements for the medical user is that the user needs to mix the liquid monomer component and the powder component in a mixing system or in crucibles right before applying the cement. Mixing errors can easily occur in the process and adversely affect the quality of the cement. Moreover, the components must be mixed rapidly. In this context, it is important to mix all of the cement powder and monomer component without forming lumps and prevent the introduction of air bubbles during the mixing process. Unlike manual mixing, the use of vacuum mixing systems prevents the formation of air bubbles in the cement dough to a large extent. Examples of mixing systems are disclosed in patent specifications U.S. Pat. No. 4,015,945, EP-A-0 674 888, and JP 2003-181270. However, vacuum mixing systems necessitate an additional vacuum pump and are therefore relatively expensive. Moreover, depending on the type of cement concerned, a certain waiting time is required after mixing the monomer component and the powder component until the cement dough is tack-free and can be applied. Because of the large variety of errors that can occur while mixing conventional PMMA bone cements, appropriately trained personnel is required for this purpose. The corresponding training is associated with considerable expenses. Moreover, mixing of the liquid monomer component and the powder component is associated with exposure of the user to monomer vapours and particles released from the powder-like cement.

Paste-like polymethylmethacrylate bone cements have been described as an alternative to the conventional powder-liquid polymethylmethacrylate bone cements in unexamined German patent applications DE-A-10 2007 052 116, DE-A-10 2007 050 762, and DE-A-10 2007 050 763. Said bone cements are provided to the user in the form of pre-mixed pastes that are stable during storage. Said pastes each contain one methacrylate monomer for radical polymerisation, one polymer that is soluble in said methacrylate polymer, and one particulate polymer that is insoluble in said methacrylate monomer (since both pastes contain an insoluble particulate polymer, systems of this type are called "symmetrical"). In addition, one of said pastes contains a radical polymerisation initiator, whereas the other paste comprises a polymerisation activator. As a result of the selected composition, the bone cement produced from said pastes possesses sufficiently high viscosity and cohesion in order to withstand the pressure from bleeding until it is fully cured. When the two pastes are mixed, the polymerisation initiator reacts with the accelerator to form radicals that initiate the radical polymerisation of the methacrylate monomers. Owing to the advancing polymerisation, the paste is cured while the methacrylate monomers are consumed. It has been found that, even if highly cross-linked poly(methacrylate) particles are used as particulate polymer that is insoluble in the methacrylate monomer, these take up and enclose small fractions of methacrylate monomer and compounds dissolved therein. This causes the insoluble polymer particles of the one paste to contain inclusions of monomer liquid and initiator dissolved therein, whereas the insoluble polymer particles of the other paste in turn contain inclusions of monomer liquid and accelerator dissolved therein. After the two pastes are mixed, the phase consisting of the methacrylate monomer and the polymer dissolved therein, in which the insoluble polymer particles are suspended, cures while forming bone cement that is ready for application. Afterwards, the initially enclosed monomer liquid diffuses from the insoluble polymer particles and undergoes secondary polymerisation. The monomer liquid diffusing from the insoluble polymer particles acts as a plasticiser, due to the secondary polymerisation, until it is consumed. This leads to the initially cured bone cement pastes meeting the requirements of ISO 5833, but also still showing pronounced secondary curing due to secondary polymerisation of the monomer liquid diffusing from the insoluble polymer particles.

Used with conventional PMMA bone cements that consisted of a powder component and a monomer liquid, the initiator system of dibenzoylperoxide and N,N-dimethyl-p-toluidine has proven its value in general (K.-D. Kühn: Knochenzemente für die Endoprothetik: ein aktueller Vergleich der physikalischen and chemischen Eigenschaften handelsüblicher PMMA-Zemente. Springer-Verlag Berlin Heidelberg New York, 2001). In this context, dibenzolyperoxide is present as a solid in the cement powder and N,N-dimethyl-p-toluidine is dissolved in the monomer component. However, our experiments with cement pastes using the dibenzoylperoxide/N,N-dimethyl-p-toluidine initiator system demonstrated that pastes containing N,N-dimethyl-p-toluidine have a pronounced tendency to polymerise spontaneously. Moreover, the accelerator, N,N-dimethyl-p-toluidine, that has proven its value with conventional powder/liquid polymethylmethacrylate bone cements has been the subject of some criticism due to its toxicological properties.

Aside from these redox systems, initiator systems based on the use of barbiturates have also been described. DE-A-1 495 520 describes a method for polymerisation of vinyl compounds and polyesters. In said method, barbituric acid derivatives, halide ion donors, and copper compounds are dissolved in the monomer or mixture of monomers. In this context, the combination of barbituric acid derivative, halide ion donor, and copper compound initiates the polymerisation. It is also feasible to add organic peroxides or hydrogen peroxide. Our own experiments in this context showed that initiation is also feasible in the absence of atmospheric oxygen or peroxides, which is contrary to the assumption made in DE-A-1 495 520, according to which air or peroxides are required to trigger polymerisation by barbiturate in the presence of copper ions and chloride ions. This means that the barbiturate itself obviously acts as initiator.

A somewhat more complex system is described in DE-A-10 2007 050 763 and DE-A-10 2007 050 763. In this system, earth alkali salts of barbiturates and basic copper salts are contained in one paste. These two salts are insoluble in the methacrylate monomer. A weak organic acid such as 2-ethylhexanoic acid is present in a second paste. In addition, the pastes contain a chloride ion donor, preferably tetraalkylammonium chloride is used as chloride ion donor. Mixing the two pastes, the weak organic acid simultaneously converts both the barbiturate into the soluble acid form and copper into a soluble copper salt. The advantage of this system, in particular in the case of pastes with multi-functional monomers, is that earlier diffusion and ion exchange processes allow the processing time to be increased which otherwise is very short, usually on the order of seconds, where multi-functional monomers are used. The use of tetraalkylammonium chloride as chloride ion donor in the initiator system described in DE-A-10 2007 050 762 and DE-A-10 2007 050 763 is disadvantageous though, since said substance can trigger spontaneous polymerisation in the presence of dissolved heavy metal salts.

The present invention was based on the object to overcome the disadvantages of the prior art concerning bone cement systems that are based on at least two pastes.

The present invention was therefore based, in particular, on the object to provide a kit based on two pastes that is designed for producing bone cement having high initial stability and therefore low post-cure. Moreover, while still separated from each other, the pastes should feature the highest possible stability against polymerisation (i.e. should show no tendency to undergo spontaneous polymerisation, if possible).

A kit comprising a paste A and a paste B contributes to a solution meeting the object specified above,
whereby
(a) paste A contains
 (a1) at least one monomer for radical polymerisation; and
 (a2) at least one barbituric acid derivative as polymerisation initiator;
(b) paste B contains
 (b1) at least one monomer for radical polymerisation; and
 (b2) at least one heavy metal compound as polymerisation accelerator that is selected from the group consisting of heavy metal salts and heavy metal complexes;
and whereby
i) paste B contains less than 0.01% by weight, relative to the total weight of paste B, of a peroxide;
ii) at least one of the pastes A and B contains, as component (a3) and/or (b3), at least one filling agent that is poorly soluble or insoluble in (a1) and/or (b1), respectively; and
iii) at least one of the pastes A and B contains, as component (a4) and/or (b4), at least one inorganic halide salt.

The invention is further based on the idea to use a first paste that contains a barbiturate that is soluble in a monomer for radical polymerisation, such as methyl-methacrylate. Upon said first paste being mixed with a second paste containing a heavy metal compound in addition to the monomer for radical polymerisation, the soluble barbiturate is reacts with the preferably basic heavy metal salt due to its acidity. It has been found surprisingly that this makes it feasible to initiate the polymerisation reaction in the presence of an inorganic halide ion donor that is preferably soluble in the monomer. The action of the barbiturate on the preferably basic heavy metal salt obviously converts the heavy metal ions into a soluble salt form which initiates polymerisation of the methacrylate monomer through its action on barbituric acid. In this context, the use of aromatic amines and quaternary ammonium chlorides as accelerators is no longer required.

According to the invention, a kit shall be understood to be a system made up of at least two components. Although reference to two components (i.e. paste A and paste B) is made in the following, the kit can just as well contain more than two components, for example three, four, five or more than five components, according to need. The individual components preferably are provided to be packaged separate from each other such that the ingredients of the one kit component do not contact the ingredients of another kit component. Accordingly, it is feasible, for example, to package the respective kit components separate from each other and to store them together in a reservoir container.

Paste A contains, as component (a1), a monomer for radical polymerisation, whereby this is preferably a monomer that is liquid at a temperature of 25° C. and a pressure of 1,013 hPa.

Preferably, the monomer (a1) for radical polymerisation is a methacrylate monomer, in particular a methacrylic acid ester. Preferably, the methacrylic acid ester (a1) is a monofunctional methacrylic acid ester. Preferably, said substance is hydrophobic. The use of hydrophobic monofunctional methacrylic acid esters (a1) allows later enlargement of the volume of the bone cement due to the uptake of water and thus damage to the bone to be prevented. According to a preferred embodiment, the monofunctional methacrylic acid ester is hydrophobic if it contains no further polar groups aside from the ester group. The monofunctional hydrophobic methacrylic acid ester preferably comprises no carboxyl groups, hydroxyl groups, amide groups, sulfonic acid groups, sulfate groups, phosphate groups or phosphonate groups.

The esters preferably are alkyl esters. According to the invention, cycloalkyl esters are also included in alkyl esters. According to a preferred embodiment, the alkyl esters are esters of methacrylic acid and alcohols comprising 1 to 20 carbon atoms, more preferably 1 to 10 carbon atoms, even more preferably 1 to 6 carbon atoms, and particularly preferably 1 to 4 carbon atoms. The alcohols can be substituted or non-substituted and preferably are non-substituted. Moreover, the alcohols can be saturated or unsaturated and preferably are saturated.

According to a particularly preferred embodiment, the monomer (a1) for radical polymerisation is a methacrylic acid methylester, methacrylic acid ethylester or a mixture of said two monomers.

According to a further preferred embodiment, the monomer (a1) for radical polymerisation is not a bisphenol A-derived methacrylic acid ester.

The monomer (a1) for radical polymerisation used according to the invention preferably has a molar mass of less than 1,000 g/mol. This also comprises monomers for radical polymerisation that are components of a mixture of monomers, whereby at least one of the monomers for radical polymerisation of the mixture of monomers has a defined structure with a molar mass of less than 1,000 g/mol.

The monomer (a1) for radical polymerisation is preferably characterised in that an aqueous solution of the monomer (a1) for radical polymerisation has a pH in the range of 5 to 9, preferably in the range of 5.5 to 8.5, even more preferably in the range of 6 to 8, and particularly preferably in the range of 6.5 to 7.5.

Paste A preferably contains 15 to 85% by weight, more preferably 20 to 70% by weight, even more preferably 25 to 60% by weight, and particularly preferably 25 to 50% by weight, each relative to the total weight of paste A, of the at least one monomer (a1) for radical polymerisation.

Moreover, paste A contains, as component (a2), at least one barbituric acid derivative as polymerisation initiator, whereby the barbituric acid derivative is preferably selected from the group consisting of 1-mono-substituted barbiturates, 5-mono-substituted barbiturates, 1,5-di-substituted barbiturates, 1,3,5-tri-substituted barbiturates, and 1,3,5-tetra-substituted barbiturates. According to a particular refinement of the kit according to the invention, the barbituric acid derivative is selected from the group consisting of 1,5-di-substituted barbiturates, 1,3,5-tri-substituted barbiturates, and 1,3,5-tetra-substituted barbiturates.

According to a preferred embodiment, the barbituric acid derivative (a2) is soluble in the monomer (a1) for radical polymerisation. The barbituric acid derivative (a2) is soluble in the monomer (a1) for radical polymerisation of at least 1 g/l, preferably at least 3 g/l, even more preferably at least 5 g/l, and particularly preferably at least 10 g/l of the barbituric acid derivative (a2) dissolve(s) in the monomer (a1) for radical polymerisation at a temperature of 25° C.

There is no limitation with regard to the type of substituents on the barbituric acid. The substituents can, for example, be aliphatic or aromatic substituents. In this context, alkyl, cycloalkyl, allyl or aryl substituents can be preferred. The substituents can also include hetero atoms. In particular, the substituents can be thiol substituents. Accordingly, 1,5-disubstituted thiobarbiturates or 1,3,5-trisubstituted thiobarbiturates can be preferred.

According to a preferred embodiment, the substituents each have a length of 1 to 10 carbon atoms, more preferably a length of 1 to 8 carbon atoms, and particularly preferably a length in the range of 2 to 7 carbon atoms.

Barbiturates having one substituent each at position 1 and position 5, one substituent each at positions 1, 3, and 5 or one substituent each at positions 1 and 3 and two substituents at position 5 are preferred according to the invention.

According to another preferred embodiment, the barbituric acid derivative is a 1,5-disubstituted barbiturate or a 1,3,5-trisubstituted barbiturate. According to a particularly preferred embodiment, the barbituric acid derivative (a2) is selected from the group consisting of 1-cyclohexyl-5-ethyl-barbituric acid, 1-phenyl-5-ethyl-barbituric acid, and 1,3,5-trimethyl-barbituric acid.

Preferably, paste A contains an amount of the at least one barbituric acid derivative (a2) in a range of 0.1 to 10% by weight, more preferably in a range of 0.5 to 8% by weight, and even more preferably in a range of 1 to 5% by weight, each relative to the total weight of paste A.

According to a particular embodiment of the kit according to the invention, the barbituric acid derivative (a2) is present in paste A in a form, in which at least 50 mol-%, particularly preferably at least 75 mol-%, and most preferably at least 95 mol-% of the barbituric acid derivative (a2) are present in the form of the protonated acid. It is preferred, in particular, in this context that the barbituric acid derivative (a2) is not a salt of the barbituric acid derivative, in particular is not a calcium salt of the barbituric acid derivative. Moreover, it is preferred in this context in said particular embodiment of the kit according to the invention that paste B contains less than 2% by weight, particularly preferably less than 0.5% by weight, even more preferably less than 0.1%, each relative to the total weight of paste B, of an organic acid that is soluble in the monomer (b1) for radical polymerisation, preferably an acid selected from the group consisting of 2-ethylhexanoic acid, hexanoic acid, heptanoic acid, octanoic acid, malonic acid, monomers with acid functions such as sulfonic acid, phosphoric acid, phosphonic acid, and carboxylic acid groups, acetic acid, propionic acid, pivalic acid, chloroacetic acid, methanesulfonic acid, and phosphoric acid. Most preferably, paste B contains neither of these acids.

Paste B also contains, as component (b1), a monomer for radical polymerisation, whereby this is preferably a monomer that is liquid at a temperature of 25° C. and a pressure of 1,013 hPa. The monomer (b1) for radical polymerisation contained in a kit can be identical to or different from the monomer (a1) for radical polymerisation, whereby it is preferred for the monomer (a1) for radical polymerisation and the monomer (b1) for radical polymerisation to be identical.

The monomer (b1) for radical polymerisation preferably is a methacrylate monomer, in particular a methacrylic acid ester. Preferably, the methacrylic acid ester (b1) is a monofunctional methacrylic acid ester. Preferably, said substance is hydrophobic. The use of hydrophobic monofunctional methacrylic acid esters (b1) allows later enlargement of the volume of the bone cement due to the uptake of water and thus damage to the bone to be prevented. According to a preferred embodiment, the monofunctional methacrylic acid ester is hydrophobic if it contains no further polar groups aside from the ester group. The monofunctional hydrophobic methacrylic acid ester preferably comprises no carboxyl groups, hydroxyl groups, amide groups, sulfonic acid groups, sulfate groups, phosphate groups or phosphonate groups.

The esters preferably are alkyl esters. According to the invention, cycloalkyl esters are also included in alkyl esters. According to a preferred embodiment, the alkyl esters are esters of methacrylic acid and alcohols comprising 1 to 20 carbon atoms, more preferably 1 to 10 carbon atoms, even more preferably 1 to 6 carbon atoms, and particularly preferably 1 to 4 carbon atoms. The alcohols can be substituted or non-substituted and preferably are non-substituted. Moreover, the alcohols can be saturated or unsaturated and preferably are saturated.

According to a particularly preferred embodiment, the monomer (b1) for radical polymerisation is a methacrylic acid methylester, methacrylic acid ethylester or a mixture of said two monomers.

According to a further particularly preferred embodiment, the monomer (b1) for radical polymerisation is not a bisphenol A-derived methacrylic acid ester.

The monomer (b1) for radical polymerisation used according to the invention preferably has a molar mass of less than 1,000 g/mol. This also comprises monomers for radical polymerisation that are components of a mixture of monomers, whereby at least one of the monomers for radical polymerisation of the mixture of monomers has a defined structure with a molar mass of less than 1,000 g/mol.

The monomer (b1) for radical polymerisation is characterised in that an aqueous solution of the monomer (b1) for radical polymerisation has a pH in the range of 5 to 9, preferably in the range of 5.5 to 8.5, even more preferably in the range of 6 to 8, and particularly preferably in the range of 6.5 to 7.5.

Paste B preferably contains 15 to 85% by weight, more preferably 20 to 70% by weight, even more preferably 25 to 60% by weight, and particularly preferably 25 to 50% by weight, each relative to the total weight of paste B, of the at least one monomer (b1) for radical polymerisation.

Paste B further contains, as component (b2), at least one heavy metal compound selected from the group consisting of heavy metal salts and heavy metal complexes, as polymerisation accelerator, where it has proven to be particularly advantageous for the at least one heavy metal compound (b2) to be poorly soluble, preferably even insoluble, in the monomer (b1) for radical polymerisation. A heavy metal compound (b2) is considered to be poorly soluble or insoluble in the monomer (b1) for radical polymerisation if less than 1 g/l, preferably less than 0.1 g/l, even more preferably less than 0.01 g/l, yet more preferably less than 0.001 g/l, even yet more preferably less than 0.0001 g/l, and most preferably no significant amounts of the heavy metal compound (b2) at all dissolve at a temperature of 25° C. in the monomer (b1) for radical polymerisation (i.e. the heavy metal compound (b2) is insoluble in the monomer (b1) for radical polymerisation).

According to the invention, heavy metal compounds shall be understood to mean metals with a density of at least 3.5 g/cm$^3$, preferably of at least 5 g/cm$^3$, at a temperature of 20° C.

According to a preferred embodiment, the heavy metal compound (b2) is a basic heavy metal compound. Basic heavy metal compound shall be understood to mean a heavy metal compound which, when dissolved or suspended in water, has a pH of at least 7.0, preferably at least 8, and even more preferably at least 8.5.

According to a particularly preferred embodiment, the heavy metal compounds (b2) are compounds of metals that can change their oxidation state. Copper (II), iron (II), iron (III), manganese (II), manganese (III), cobalt (II), and cobalt (III) compounds are preferred according to the invention in this context and copper(II) compounds are particularly preferred.

Provided they are heavy metal compounds that are poorly soluble or insoluble in the monomer (b1) for radical polymerisation, the heavy metal compounds according to the invention are preferably capable, in the presence of the barbituric acid derivatives (a2), of converting into a form that is soluble in the monomer (a1) and/or (b1) for radical polymerisation.

According to the invention, the heavy metal compounds (b2) are heavy metal salts or heavy metal complexes.

The heavy metal salts (b2) preferably are halides, hydroxides, carbonates or carboxylic acid salts of heavy metals. Copper (II), iron (II), iron (III), manganese (II), manganese (III), cobalt (II), and cobalt (III) salts are preferred heavy metals salts.

Moreover, halide salts are conceivable as heavy metal compound (b2). The halide salt can preferably be selected from the group consisting of heavy metal chlorides and bromides. According to a particular embodiment, the halide salt is a compound selected from the group consisting of copper(II) chloride, manganese(II) chloride, iron(II) chloride, iron(III) chloride, cobalt(II) chloride, and cobalt(III) chloride.

According to a particularly preferred embodiment, the heavy metal salt (b2) is selected from the group consisting of copper(II) hydroxide, basic copper(II) carbonate, copper(II) chloride, copper(II) 2-ethylhexanoate or a mixture of at least two thereof, in particular a mixture of copper(II) hydroxide and copper(II) carbonate.

Preferably, paste B contains an amount of the heavy metal compound (b2) in a range of 0.0005 to 0.5% by weight, more preferably in a range of 0.001 to 0.05% by weight, and particularly preferably in a range of 0.001 to 0.01% by weight, each relative to the total weight of paste B.

According to feature i), the kit according to the invention is characterised in that paste B contains less than 0.01% by weight, particularly preferably less than 0.001% by weight, and most preferably less than 0.0001% by weight, each relative to the total weight of paste B, of a peroxide. According to a particular embodiment of the kit according to the invention both paste A and paste B contain less than 0.01% by weight, particularly preferably less than 0.001% by weight, and most preferably less than 0.0001% by weight, each relative to the total weight of paste A and/or paste B, respectively, of a peroxide. It is most preferred for neither paste A nor paste B to contain a peroxide. According to the invention, a peroxide is understood to mean compounds that contain at least one peroxo group (—O—O—).

Moreover, according to feature ii), the kit according to the invention is characterised in that at least one of the pastes A and B contains, as component (a3) or (b3), at least one filling agent that is poorly soluble or insoluble in (a1) and/or (b1), respectively. Provided one of the pastes contains a poorly soluble or insoluble filling agent and the other paste contains no poorly soluble or insoluble filling agent at all or contains a negligible amount of poorly soluble or insoluble filling agent as compared to the amount present in the other paste, the kit is called "asymmetrical". In contrast, a so-called "symmetrical" kit has approximately comparable amounts of the poorly soluble or insoluble filling agent present in both pastes.

The poorly soluble or insoluble filling agent (a3) (in case of paste A) and/or (b3) (in case of paste B) is a solid substance at room temperature and capable of increasing the viscosity of the mixture composed of the remaining ingredients contained in paste A and/or paste B, respectively. The filling agent (a3) and/or (b3) should be biocompatible.

According to a preferred embodiment, the poorly soluble or insoluble filling agent (a3) and/or (b3) is selected from polymers, inorganic salts, inorganic oxides, metals, and metal alloys.

Preferably, the poorly soluble or insoluble filling agent (a3) and/or (b3) is particulate. According to a particularly preferred embodiment, the poorly soluble or insoluble filling agent (a3) and/or (b3) has an average particle size in the range of 10 nm to 100 μm and particularly preferably in the range of 100 nm to 10 p.m. The average particle size shall be understood herein to mean a size range that applies to at least 90 percent of the particles.

In the scope of the invention, the term, polymers, shall include both homopolymers and copolymers.

The polymer used as poorly soluble or insoluble filling agent (a3) and/or (b3) preferably is a polymer with a mean (by weight) molar mass of at least 150,000 g/mol. The specification of the molar mass refers to the molar mass determined by viscosimetry. The polymer can, for example, be a polymer or copolymer of a methacrylic acid ester. According to a particularly preferred embodiment, the at least one polymer is selected from the group consisting of polymethacrylic acid methylester (PMMA), polymethacrylic acid ethylester (PMAE), polymethacrylic acid propylester (PMAP), polymethacrylic acid isopropylester, poly(methylmethacrylate-co-methylacrylate), and poly(styrene-co-methylmethacrylate). However, the polymer can just as well be selected from the group consisting of polyethylene, polypropylene or polybutadiene. Moreover, the polymer can be cross-linked or non-cross-linked with cross-linked polymers being preferred. In this context, the cross-linking is effected through a difunctional compound. The difunctional compound can be selected, for example, from the group consisting of alkylene glycol dimethacrylates. An expedient cross-linker is, for example, ethylene glycol dimethacrylate.

The inorganic salt that can be used as poorly soluble or insoluble filling agent (a3) and/or (b3) can be a salt that is soluble or insoluble in the monomer (a1) and/or (b1) for radical polymerisation. Preferably, the inorganic salt is a salt of an element selected from the second main group of the periodic system of elements.

According to a preferred embodiment, the inorganic salt is a calcium, strontium or barium salt. According to a particularly preferred embodiment, the inorganic salt is calcium sulfate, barium sulfate or calcium carbonate.

The inorganic oxide that can be used as poorly soluble or insoluble filling agent (a3) and/or (b3) can preferably be a metal oxide. According to a preferred embodiment, the inorganic oxide is a transition metal oxide. According to a particularly preferred embodiment, the inorganic oxide is titanium dioxide or zirconium dioxide.

The metal that can be used as poorly soluble or insoluble filling agent (a3) and/or (b3) can, for example, be a transition metal. According to a preferred embodiment, the metal is tantalum or tungsten.

The metal alloy that can be used as poorly soluble or insoluble filling agent (a3) and/or (b3) is an alloy of at least two metals. Preferably, the alloy contains at least one transition metal. According to a particularly preferred embodiment, the alloy comprises at least tantalum or tungsten. The alloy can also be an alloy of tantalum and tungsten.

The filling agent (a3) and/or (b3) is poorly soluble or insoluble in the monomer (a1) and/or (b1) for radical polymerisation, respectively. According to the invention, the filling agent (a3) and/or (b3) is considered to be poorly soluble or insoluble in the monomer (a1) and/or (b1) for radical polymerisation, respectively, if the solubility of the filling agent (a3) and/or (b3) in the monomer (a1) and/or (b1), respectively, at a temperature of 25° C. is less than 50 g/l, preferably less than 25 g/l, more preferably less than 10 g/l, even more preferably less than 5 g/l, and yet more preferably less than 0.5 g/l, whereby it is most preferred that the poorly soluble or insoluble filling agent (a3) and/or (b3) does not dissolve at all or only in negligible amounts in the monomer (a1) and/or (b1) for radical polymerisation, respectively.

It is particularly preferred according to the invention that the at least one polymer that is poorly soluble or insoluble in (a1) and/or (b1) is selected from the group consisting of cross-linked poly(methylmethacrylate-co-methylacrylate), cross-linked poly(methylmethacrylate), and a mixture of said two polymers.

Moreover, according to feature iii), the kit according to the invention is characterised in that at least one of the pastes A and B, particularly preferably paste B and in particular paste B exclusively, contains, as component (a4) and/or (b4), at least one inorganic halide salt, whereby it has proven to be advantageous for said inorganic halide salt (a4) and/or (b4) to be at least partially soluble in the monomer (a1) and/or (b1) for radical polymerisation, respectively. Preferably, an inorganic halide salt (a4) and/or (b4) is considered to be at least partially soluble in the monomer (a1) and/or (b1) for radical polymerisation, respectively, if its solubility in the polymerisable monomer that is present in the same paste as the halide salt is at least 0.001 g/l, more preferably at least 0.01 g/l, even more preferably at least 0.1 g/l, and yet more preferably at least 1 g/l.

Preferably, the at least one inorganic halide salt (a4) and/or (b4) is a halide salt made up by at least one halide anion and one metal cation or one metal oxide cation, whereby $F^-$, $Cl^-$, and $Br^-$ are conceivable as halide anion and $CL^-$ is particularly preferred. Preferably, the at least one inorganic halide salt (a4) and/or (b4) is selected from the group consisting of an alkali halide, an earth alkali halide, a heavy metal halide, a heavy metal oxide halide, ammonium chloride, and a mixture of at least two of said halide salts. Preferred halide salts include lithium chloride, sodium chloride, potassium chloride, calcium chloride, magnesium chloride, and ammonium chloride. Halide salts, in particular chlorides, of zinc ($Zn^{2+}$) and zirconium ($Zr^{4+}$) can also be used as halide salts. Zirconium oxide cation, $ZrO^{2+}$, for example, can be a preferred metal oxide cation in this context. For example, the inorganic halide salt is zinc dichloride ($ZnCl_2$) or zirconiumoxide dichloride ($ZrOCl_2$). According to the invention, lithium chloride and zirconiumoxide dichloride ($ZrOCl_2$) are particularly preferred as inorganic halide salt (a4) and/or (b4), whereby the use of lithium chloride is most preferred.

According to a first particular refinement of the kit according to the invention, paste B does not contain 40 mg lithium chloride per 36.099 g of paste B. Accordingly, the fraction of lithium chloride in this embodiment is not 0.1108% by weight, relative to the total weight of paste B.

According to a second particular refinement of the kit according to the invention, paste B does not contain 2 mg copper(II) hydroxide per 36.099 g of paste B. Accordingly, the fraction of copper(II) hydroxide in this embodiment is not 0.00554% by weight, relative to the total weight of paste B. In particular, paste B contains more than 0.00554% by weight, particularly preferably more than 0.0075% by weight, and even more preferably more than 0.01% by weight of the heavy metal compound (b2), each relative to the total weight of paste B, in said second particular refinement of the kit according to the invention.

According to a third particular refinement of the kit according to the invention, paste B does not contain the heavy metal compound (b2) and the inorganic halide salt (b4) at a relative mass ratio of heavy metal compound (b2):inorganic halide salt (B4) of 1:20. In particular, in said third particular refinement of the kit according to the invention, paste B contains the heavy metal compound (b2) and the inorganic halide salt (b4) at a relative mass ratio of heavy metal compound (b2):inorganic halide salt (B4) of more than 1:20, preferably of more than 1:10.

Moreover, it is preferred in this context that paste A or paste B or paste A and paste B contain an amount of the at least one inorganic halide salt (a4) and/or (b4) in a range of 0.001 to 7.5% by weight, more preferably in a range of 0.01 to 5% by weight, even more preferably in a range of 0.1 to 2.5% by weight, and most preferably in a range of 0.5 to 1.5% by weight, each relative to the total weight of paste A and/or paste B, respectively.

Moreover, according to the invention, paste A, paste B or paste A and paste B can contain a polymer (a5) and/or (b5) that is soluble in (a1) and/or (b1), respectively.

According to the invention, said polymer (a5) and/or (b5) is soluble in the polymerisable monomer contained in the paste that contains the soluble polymer as well, if at least 10 g/l, preferably at least 25 g/l, more preferably at least 50 g/l, and particularly preferably at least 100 g/l of the polymer dissolve in said polymerisable monomer. The polymer (a5) and/or (b5) that is soluble in the polymerisable monomer (a1) and/or (b1), respectively, can be a homopolymer or a copolymer. Said polymer (a5) and/or (b5) preferably is a polymer with a mean (by weight) molar mass of at least 150,000 g/mol. The polymer (a5) and/or (b5) can, for example, be a polymer or copolymer of a methacrylic acid ester. According to a particularly preferred embodiment, the at least one soluble polymer (a5) and/or (b5) is selected from the group consisting of polymethacrylic acid methylester (PMMA), polymethacrylic acid ethylester (PMAE), polymethacrylic acid propylester (PMAP), polymethacrylic acid isopropylester, poly(methylmethacrylate-co-methylacrylate), poly(styrene-co-methylmethacrylate), and a mixture of at least two of said polymers.

The amount of the polymer (a5) and/or (b5) that is soluble in the monomer (a1) and/or (b1) for radical polymerisation, respectively, that is present in the paste containing said polymer depends on whether or not the corresponding paste contains a filling agent (a3) and/or (b3) that is insoluble in the monomer (a1) and/or (b1) for radical polymerisation, respectively. Usually, the amount of the polymer (a5) and/or (b5) that is soluble in the monomer (a1) and/or (b1) for radical polymerisation, respectively, that is present in the paste containing said polymer is in a range of 1 to 85% by weight, relative to the total weight of the paste containing said soluble polymer.

Pastes A and B can contain further components aside from the components explained above. Said further components can each be present either in paste A, in paste B or in paste A and paste B.

According to a preferred embodiment, at least one radio-opaquer is present in at least one of the pastes A and B. The radio-opaquer can be a common radio-opaquer in this field. Suitable radio-opaquers can be soluble or insoluble in the monomer (a1) for radical polymerisation or the monomer (b1) for radical polymerisation. The radio-opaquer is preferably selected from the group consisting of metal oxides (such as, for example, zirconium oxide), barium sulfate, toxicologically acceptable heavy metal particles (such as, for example, tantalum), ferrite, magnetite (supramagnetic magnetite also, if applicable), and biocompatible calcium salts. Said radio-opaquers preferably have a mean particle diameter in the range of 10 nm to 500 μm. Moreover, conceivable radio-opaquers also include esters of 3,5-bis(acetamido)-2,4,6-tri-iodobenzoic acid, gadolinium compounds, such as gadolinium chelate involving the esters of 1,4,7,10-tetraazacyclododecan-1,4,7,10-tetraacetic acid (DOTA).

According to another preferred embodiment, at least one of the pastes A and B contains at least one colourant. The colourant can be a common colourant in this field and preferably can be a food colourant. Moreover, the colourant can be soluble or insoluble in the at least one monomer (a1) for radical polymerisation or the at least one monomer (a2) for radical polymerisation. According to a particularly preferred embodiment, the colourant is selected from the group consisting of E101, E104, E132, E141 (chlorophyllin), E142, riboflavin, and lissamine green. According to the invention, the term, colourant, shall also include colour varnishes, such as, for example, colour varnish green, the aluminium salt of a mixture of E104 and E132.

According to another preferred embodiment, at least one of the pastes A and B contains at least one pharmaceutical agent. The at least one pharmaceutical agent can be present in at least one of pastes A and B in dissolved or suspended form.

The pharmaceutical agent can preferably be selected from the group consisting of antibiotics, antiphlogistic agents, steroids, hormones, growth factors, bisphosphonates, cytostatic agents, and gene vectors. According to a particularly preferred embodiment, the at least one pharmaceutical agent is an antibiotic.

Preferably, the at least one antibiotic is selected from the group consisting of aminoglyoside antibiotics, glycopeptide antibiotics, lincosamide antibiotics, gyrase inhibitors, carbapenems, cyclic lipopeptides, glycylcyclines, oxazolidones, and polypeptide antibiotics.

According to a particularly preferred embodiment, the at least one antibiotic is a member selected from the group consisting of gentamicin, tobramycin, amikacin, vancomycin, teicoplanin, dalbavancin, lincosamine, clindamycin, moxifloxacin, levofloxacin, ofloxacin, ciprofloxacin, doripenem, meropenem, tigecycline, linezolide, eperezolide, ramoplanin, metronidazole, timidazole, omidazole, and colistin, as well as salts and esters thereof.

Accordingly, the at least one antibiotic can be selected from the group consisting of gentamicin sulfate, gentamicin hydrochloride, amikacin sulfate, amikacin hydrochloride, tobramycin sulfate, tobramycin hydrochloride, clindamycin hydrochloride, lincosamine hydrochloride, and moxifloxacin.

The at least one antiphlogistic agent is preferably selected from the group consisting of non-steroidal antiphlogistic agents and glucocorticoids. According to a partitularly preferred embodiment, the at least one antiphlogistic agent is selected from the group consisting of acetylsalicylic acid, ibuprofen, diclofenac, ketoprofen, dexamethasone, prednisone, hydrocortisone, hydrocortisone acetate, and fluticasone.

The at least one hormone is preferably selected from the group consisting of serotonin, somatotropin, testosterone, and estrogen.

Preferably, the at least one growth factor is selected from the group consisting of Fibroblast Growth Factor (FGF), Transforming Growth Factor (TGF), Platelet Derived Growth Factor (PDGF), Epidermal Growth Factor (EGF), Vascular Endothelial Growth Factor (VEGF), insulin-like growth factors (IGF), Hepatocyte Growth Factor (HGF), Bone Morphogenetic Protein (BMP), interleukin-1B, interleukin 8, and nerve growth factor.

The at least one cytostatic agent is preferably selected from the group consisting of alkylating agents, platinum analogues, intercalating agents, mitosis inhibitors, taxanes, topoisomerase inhibitors, and antimetabolites.

The at least one bisphosphonate is preferably selected from the group consisting of zoledronate and aledronate.

According to another preferred embodiment, at least one of the pastes A and B contains at least one biocompatible elastomer. Preferably, the biocompatible elastomer is particulate. Preferably, the biocompatible elastomer is soluble in the at least one monomer (a1) for radical polymerisation or the at least one monomer (b1) for radical polymerisation. The use of butadiene as biocompatible elastomer has proven to be particularly well-suited.

According to another preferred embodiment, at least one of the pastes A and B contains at least one monomer with adsorption groups. An amide group can, for example, be an adsorption group. Accordingly, the monomer with adsorption group can, for example, be methacrylic acid amide. Using at least one monomer with adsorption groups would allow the binding of the bone cement to articular endoprostheses to be influenced in a targeted manner.

According to another preferred embodiment, at least one of the pastes A and B contains at least one stabiliser. The stabiliser should be suitable to prevent spontaneous polymerisation of the monomers (a1) and/or (b1) for polymerisation that are present in pastes A and B. Moreover, the stabiliser should not undergo interfering interactions with the other components contained in the pastes. Stabilisers of said type are known according to the prior art. According to a preferred embodiment, the stabiliser is 2,6-di-tert-butyl-4-methylphenol and/or 2,6-di-tertbutyl-phenol.

According to a first particular refinement of the kit according to the invention, the kit is an "asymmetrical" kit. It is preferred in this context that paste A contains 20 to 70% by weight, particularly preferably 25 to 60% by weight, even more preferably 30 to 55% by weight, and most preferably 34 to 47% by weight, each relative to the total weight of paste A, of the filling agent (a3) that is insoluble in (a1), and paste B contains less than 5% by weight, particularly preferably less than 1% by weight, even more preferably less than 0.1% by weight, and yet more preferably less than 0.01% by weight, each relative to the total weight of paste B, of the filling agent (b3) that is insoluble in (b1), whereby it is most preferred that paste B contains no filling agent (b3) that is insoluble in (b1) at all.

Moreover, in the context of said first particular refinement of the kit according to the invention, it is preferred that paste A contains an amount of a polymer (a5) that is soluble in (a1) in a range of 1 to 25% by weight, particularly preferably in a range of 2 to 20% by weight, even more preferably in a range of 2 to 18% by weight, and most preferably in a range of 3 to 16% by weight, each relative to the total weight of paste A, and paste B contains an amount of a polymer (b5) that is soluble in (b1) in a range of 25 to 85% by weight, particularly preferably in a range of 35 to 85% by weight, even more preferably in a range of 40 to 80% by weight, and most preferably in a range of 50 to 75% by weight, each relative to the total weight of paste B.

Moreover, it is preferred in the context of said first particular refinement of the kit according to the invention that the weight ratio of filling agent (b3) that is insoluble in (b1) to the at least one polymer (b5) that is soluble in (b1) is no more than 0.2, more preferably no more than 0.15, even more preferably no more than 0.1, yet more preferably no more than 0.05, particularly preferably no more than 0.02, and even more particularly preferably is equal to 0.

According to a second particular refinement of the kit according to the invention, the kit is a "symmetrical" kit. It is preferred in this context that paste A contains 15 to 85% by weight, particularly pref-erably 15 to 80% by weight, and even more preferably 20 to 75% by weight, each relative to the total weight of paste A, of the filling agent (a3) that is insoluble in (a1), and paste B contains 15 to 85% by weight, particularly preferably 15 to 80% by weight, and even more preferably 20 to 75% by weight, each relative to the total weight of paste B, of the filling agent (b3) that is insoluble in (b1).

Moreover, in the context of said second particular refinement of the kit according to the invention, it is preferred that paste A contains an amount of a polymer (a5) that is soluble in (a1) in a range of 5 to 50% by weight, particularly preferably in a range of 10 to 40% by weight, and even more preferably in a range of 20 to 30% by weight, each relative to the total weight of paste A, and/or paste B contains an amount of a polymer (b5) that is soluble in (b1) in a range of 5 to 50% by weight, particularly preferably in a range of 10 to 40% by weight, and even more preferably in a range of 20 to 30% by weight, each relative to the total weight of paste B.

According to the invention, the purpose of the kit containing at least pastes A and B is the production of bone cement.

For this purpose, the at least two pastes A and B are mixed with each other, upon which another paste, paste C, is obtained.

The mixing ratio preferably is 0.5 to 1.5 parts by weight of paste A and 0.5 to 1.5 parts by weight of paste B. According to a particularly preferred embodiment, the fraction of paste A is 30 to 70% by weight and the fraction of paste B is 30 to 70% by weight, each relative to the total weight of pastes A and B, respectively.

The mixing process can involve common mixing devices, for example a static mixer or a dynamic mixer.

The mixing process can proceed in a vacuum. However, the use of the initiator system according to the invention also allows for mixing of pastes A and B in the absence of a vacuum without adverse effect on the properties of the bone cement.

Paste C that is ultimately obtained after mixing the pastes of the kit is tack-free according to the ISO 5833 standard and can be processed without delay.

The bone cement generated from paste C by curing attains high strength approximately six to eight minutes after mixing the pastes contained in the kit.

According to a preferred embodiment, the kit according to the invention can be used for mechanical fixation of articular endoprostheses, for covering skull defects, for filling bone cavities, for femuroplasty, for vertebroplasty, for kyphoplasty, for the manufacture of spacers, and for the production of carrier materials for local antibiotics therapy.

In this context, the term, "spacer", shall be understood to mean implants that can be used temporarily in the scope of the two-step exchange of prostheses in septic revision surgeries.

Carrier materials for local antibiotics therapy can be provided as spheres or sphere-like bodies or as bean-shaped bodies. Besides, it is also feasible to produce rod-shaped or disc-shaped carrier materials that contain bone cement made from the kit according to the invention. Moreover, the carrier materials can also be threaded onto absorbable or non-absorbable suture material in a bead-like manner.

The uses according to the invention of bone cement described above are known from the literature and have been described therein on numerous occasions.

According to the invention, the kit is used for the above-described uses in that, preferably, the pastes contained in the kit are mixed with each other to produce a paste that is then used in the above-described uses just like pastes known from the prior art.

The invention shall be illustrated through the examples described in the following, though without limiting the scope of the invention.

EXEMPLARY EMBODIMENTS

The chemicals used in examples A1-12 and B1-14 were of analytical grade purity and were procured from wholesale chemicals sources.

Moreover, a polymethylmethacrylate-co-methylacrylate with a molar mass of <500,000 g/mol was used as soluble polymer (a5) and/or (b5). Furthermore, an ethylene glycol dimethacrylate-cross-linked polymethylmethacrylate of sieve fraction <70 µm was used as insoluble filling agent (a3) and/or (b3). Gentamicin sulfate (Fujian Fukang Ltd.) having an activity coefficient of AK=620 was also used.

Each of the pastes A1 to A12 and B1 to B14 were produced by weighing the methylmethacrylate (component (a1) and/or (b1)) in an inert plastic vessel. All of the solid components were weighed in a separate wide-neck plastic bottle with a screw cap. Three porcelain beads each were added. Then, the mixtures were homogenised for 1 hour using a tumbler-mixer. The homogenised powder components were subsequently added to the methylmethacrylate added earlier. The resulting mixtures were then mixed thoroughly. This produced pastes that were stored at room temperature over night before mixing until the final stage of swelling had been reached and spreadable pastes had formed.

| Paste A | | | | | | |
|---|---|---|---|---|---|---|
| Composition [g] | | | | | | |
| | Examples | | | | | |
| | A1 | A2 | A3 | A4 | A5 | A6 |
| Soluble polymethylmethacrylate (a5) | 6.0 | 6.0 | 6.0 | 6.0 | 6.0 | 6.0 |
| Particulate polymethylmethacrylate (a3) | 16.5 | 17.0 | 14.0 | 15.0 | 14.5 | 15.5 |
| Methylmethacrylate (a1) | 19.0 | 19.0 | 19.0 | 19.0 | 19.0 | 19.0 |
| 1-Cyclohexyl-5-ethylbarbituric acid (a2) | 2.0 | 1.5 | 2.0 | 2.0 | 1.5 | 1.5 |
| Gentamicin sulfate | — | — | 2.0 | 1.0 | 2.0 | 1.0 |
| Aerosil 300 | 0.4 | 0.4 | 0.4 | 0.4 | 0.4 | 0.4 |

-continued

Paste A

| Composition [g] Examples | A7 | A8 | A9 | A10 | A11 | A12 |
|---|---|---|---|---|---|---|
| Soluble polymethyl-methacrylate (a5) | 6.0 | 6.0 | 6.0 | 6.0 | 11.5 | 11.5 |
| Particulate poly-methylmethacrylate (a3) | 13.0 | 13.0 | 11.0 | 12.0 | 8.0 | 8.5 |
| Methylmethacrylate (a1) | 17.0 | 17.0 | 17.0 | 17.0 | 19.0 | 10.0 |
| Zirconium dioxide | 5.0 | — | 5.0 | — | 2.5 | — |
| Barium sulfate | — | 5.0 | — | 5.0 | — | 2.5 |
| 1-Cyclohexyl-5-ethylbarbituric acid (a2) | 2.0 | 2.0 | 2.0 | 2.0 | 2.0 | 1.5 |
| Gentamicin sulfate | — | — | 2.0 | 1.0g | — | 0.5 |
| Aerosil 300 | 0.4 | 0.4 | 0.4 | 0.4 | 0.4 | 0.4 |

Paste B

| Composition [g] Examples | B1 | B2 | B3 | B4 | B5 | B6 |
|---|---|---|---|---|---|---|
| Soluble polymethyl-methacrylate (b5) | 17.0 | 17.0 | 17.0 | 17.0 | 17.0 | 17.0 |
| Methylmethacrylate (b1) | 21.0 | 21.0 | 21.0 | 21.0 | 21.0 | 21.0 |
| Zirconium dioxide | 5.0 | 5.0 | 5.0 | — | — | — |
| Barium sulfate | — | — | — | 5.0 | 5.0 | 5.0 |
| Copper(II) hydroxide (b2) | 0.002 | 0.004 | 0.008 | 0.002 | 0.004 | 0.008 |
| Lithium chloride (b4) | 0.04 | 0.08 | 0.08 | 0.04 | 0.08 | 0.08 |

| Composition [g] Examples | B7 | B8 | B9 | B10 | B11 | B12 |
|---|---|---|---|---|---|---|
| Soluble polymethyl-methacrylate (b5) | 17.0 | 17.0 | 17.0 | 17.0 | 17.0 | 17.0 |
| Methylmethacrylate (b1) | 22.0 | 22.0 | 22.0 | 22.0 | 22.0 | 22.0 |
| Zirconium dioxide | 5.0 | 5.0 | 5.0 | — | — | — |
| Barium sulfate | — | — | — | 5.0 | 5.0 | 5.0 |
| Copper(II) hydroxide-copper(II) carbonate (b2) | 0.004 | 0.008 | 0.016 | 0.004 | 0.008 | 0.016 |
| Lithium chloride (b4) | 0.04 | 0.08 | 0.08 | 0.04 | 0.08 | 0.08 |

| Composition [g] Examples | B13 | B14 |
|---|---|---|
| Soluble polymethyl-methacrylate (b5) | 11.5 | 11.5 |
| Particulate poly-methylmethacrylate (b3) | 10.0 | 10.0 |
| Methylmethacrylate (b1) | 19.0 | 19.0 |
| Zirconium dioxide | 2.5 | — |
| Barium sulfate | — | 2.5 |
| Copper(II) hydroxide (b2) | 0.002 | 0.004 |
| Lithium chloride (b4) | 0.04 | 0.08 |

Pastes A1 to A12 were mixed with pastes B1 to B12, respectively, at a weight ratio of 1:1. The mixed pastes were tack-free right away. The colourless cement dough could be processed for 3.0 to 7.0 minutes. Exothermal curing proceeded in the subsequent 2 to 4 minutes In addition, pastes A1 and A12 were also kneaded together with pastes B13 and B14, respectively, at a weight ratio of 1:1. Each tack-free, colourless cement dough obtained could be processed for approx. 4 minutes and then cured during the subsequent 3 to 4 minutes.

The invention claimed is:

1. A kit comprising a paste A and a paste B, whereby
(a) paste A comprises
   (a1) at least one monomer for radical polymerisation; and
   (a2) at least one barbituric acid derivative as polymerisation initiator;
(b) paste B comprises
   (b1) at least one monomer for radical polymerisation; and
   (b2) at least one heavy metal compound as polymerisation accelerator, wherein the heavy metal compound is selected from the group consisting of copper(II) hydroxide, basic copper(II) carbonate, copper(II) chloride, copper(II) 2-ethylhexanoate or mixtures thereof;

17 wherein
i) paste B contains less than 0.01% by weight, relative to the total weight of paste B, of a peroxide;
ii) at least one of the pastes A and B contains, as component (a3) and/or (b3), at least one filling agent that is insoluble or poorly soluble in (a1) and/or (b1), respectively;
iii) at least one of the pastes A and B contains at least one inorganic halide salt as component (a4) and/or (b4), wherein the inorganic halide salt is selected from alkali halides, earth alkali halides, halide salts of zinc and zirconium and halide salts of zirconium oxide or mixtures thereof;
iv) the barbituric acid derivative (a2) is soluble in the monomer (a1) for radical polymerisation;
v) the barbituric acid derivative (a2) is selected from the group consisting of 1-mono-substituted barbiturates, 5-mono-substituted barbiturates, 1,5-di-substituted barbiturates, 1,3,5-tri-substituted barbiturates, and 1,3,5-tetra-substituted barbiturates; and
vi) paste A contains 15 to 85% by weight, relative to the total weight of paste A, of a filling agent (a3) that is insoluble or poorly soluble in (a1) and paste B contains less than 5% by weight, relative to the total weight of paste B, of a filling agent (b3) that is insoluble or poorly soluble in (b1).

2. The kit according to claim 1, whereby the at least one monomer (a1) and/or (b1) for radical polymerisation is a methacrylate monomer.

3. The kit according to claim 1 wherein paste A and paste B contain an amount of the at least one monomer (a1) and/or (b1) for radical polymerisation in a range of 15 to 85% by weight, each relative to the total weight of paste A and/or paste B, respectively.

4. The kit according to claim 1 wherein paste A contains an amount of the at least one barbituric acid derivative (a2) in a range of 0.1 to 10% by weight, relative to the total weight of paste A.

5. The kit according to claim 1 wherein paste B contains an amount of the heavy metal compound (b2) in a range of 0.0005 to 0.5% by weight, relative to the total weight of paste B.

6. The kit according to claim 1 wherein the at least one filling agent (a3) and/or (b3) that is poorly soluble or insoluble in (a1) and/or (b1), respectively, is a particulate polymer.

7. The kit according to claim 1 wherein the at least one filling agent (a3) and/or (b3) that is poorly soluble or insoluble in (a1) and/or (b1), respectively, is selected from the group consisting of cross-linked poly(methylmethacrylate-co-methylacrylate), cross-linked poly(methylmethacrylate), and a mixture of said two polymers.

8. The kit according to claim 1 wherein the at least one inorganic halide salt (a4) and/or (b4) is lithium chloride.

9. The kit according to claim 1 wherein either or both pastes A and B contain an amount of the at least one inorganic halide salt (a4) and/or (b4) in a range of 0.001 to 7.5% by weight, relative to the total weight of paste A and/or paste B, respectively.

10. The kit according to claim 1 wherein either or both pastes A and B contain a polymer (a5) and/or (b5) that is soluble in (a1) and/or (b1), respectively.

11. The kit according to claim 10, whereby the polymer (a5) and/or (b5) that is soluble in (a1) and/or (b1), respectively, is selected from the group consisting of poly(methacrylic acid methylester), poly(methacrylic acid ethylester), poly-(methylmethacrylic acid propylester), poly(methacrylic acid isopropylester), poly(methylmethacrylate-co-methylacrylate), poly(styrene-co-methylmethacrylate), and a mixture of at least two of said polymers.

18

12. The kit according to claim 1, wherein paste A contains an amount of a polymer (a5) that is soluble in (a1) in a range of 5 to 50% by weight, relative to the total weight of paste A, and paste B contains an amount of a polymer (b5) that is soluble in (b1) in a range of 5 to 50% by weight, relative to the total weight of paste B.

13. A kit comprising a paste A and a paste B, whereby
(a) paste A comprises
(a1) at least one monomer for radical polymerisation; and
(a2) at least one barbituric acid derivative as polymerisation initiator;
(b) paste B comprises
(b1) at least one monomer for radical polymerisation; and
(b2) at least one heavy metal compound as polymerisation accelerator, wherein the heavy metal compound is selected from the group consisting of copper(II) hydroxide, basic copper(II) carbonate, copper(II) chloride, copper(II) 2-ethylhexanoate or mixtures thereof;
wherein
i) paste B contains less than 0.01% by weight, relative to the total weight of paste B, of a peroxide;
ii) at least one of the pastes A and B contains, as component (a3) and/or (b3), at least one filling agent that is insoluble or poorly soluble in (a1) and/or (b1), respectively;
iii) at least one of the pastes A and B contains at least one inorganic halide salt as component (a4) and/or (b4), wherein the inorganic halide salt is selected from alkali halides, earth alkali halides, halide salts of zinc and zirconium and halide salts of zirconium oxide or mixtures thereof;
iv) the barbituric acid derivative (a2) is soluble in the monomer (a1) for radical polymerisation;
v) the barbituric acid derivative (a2) is selected from the group consisting of 1-mono-substituted barbiturates, 5-mono-substituted barbiturates, 1,5-di-substituted barbiturates, 1,3,5-tri-substituted barbiturates, and 1,3,5-tetra-substituted barbiturates; and
vi) paste A contains an amount of a polymer (a5) that is soluble in (a1) in a range of 1 to 25% by weight, relative to the total weight of paste A, and paste B contains an amount of a polymer (b5) that is soluble in (b1) in a range of 25 to 85% by weight, relative to the total weight of paste B.

14. A kit comprising a paste A and a paste B, whereby
(a) paste A comprises
(a1) at least one monomer for radical polymerisation; and
(a2) at least one barbituric acid derivative as polymerisation initiator;
(b) paste B comprises
(b1) at least one monomer for radical polymerisation; and
(b2) at least one heavy metal compound as polymerisation accelerator, wherein the heavy metal compound is selected from the group consisting of copper(II) hydroxide, basic copper(II) carbonate, copper(II) chloride, copper(II) 2-ethylhexanoate or mixtures thereof;
wherein
i) paste B contains less than 0.01% by weight, relative to the total weight of paste B, of a peroxide;
ii) at least one of the pastes A and B contains, as component (a3) and/or (b3), at least one filling agent that is insoluble or poorly soluble in (a1) and/or (b1), respectively;

iii) at least one of the pastes A and B contains at least one inorganic halide salt as component (a4) and/or (b4), wherein the inorganic halide salt is selected from alkali halides, earth alkali halides, halide salts of zinc and zirconium and halide salts of zirconium oxide or mixtures thereof;
iv) the barbituric acid derivative (a2) is soluble in the monomer (a1) for radical polymerisation;
v) the at least one barbituric acid derivative (a2) is selected from the group consisting of 1-cyclohexyl-5-ethyl-barbituric acid, 1-phenyl-5-ethyl-barbituric acid, and 1,3,5-trimethyl-barbituric acid; and
vi) paste A contains 15 to 85% by weight, relative to the total weight of paste A, of a filling agent (a3) that is insoluble or poorly soluble in (a1) and paste B contains less than 5% by weight, relative to the total weight of paste B, of a filling agent (b3) that is insoluble or poorly soluble in (b1).

15. A kit comprising a paste A and a paste B, whereby
(a) paste A comprises
  (a1) at least one monomer for radical polymerisation; and
  (a2) at least one barbituric acid derivative as polymerisation initiator;
(b) paste B comprises
  (b1) at least one monomer for radical polymerisation; and
  (b2) at least one heavy metal compound as polymerisation accelerator, wherein the heavy metal compound is selected from the group consisting of copper(II) hydroxide, basic copper(II) carbonate, copper(II) chloride, copper(II) 2-ethylhexanoate or mixtures thereof;
wherein
i) paste B contains less than 0.01% by weight, relative to the total weight of paste B, of a peroxide;
ii) at least one of the pastes A and B contains, as component (a3) and/or (b3), at least one filling agent that is insoluble or poorly soluble in (a1) and/or (b1), respectively;
iii) at least one of the pastes A and B contains at least one inorganic halide salt as component (a4) and/or (b4), wherein the inorganic halide salt is selected from alkali halides, earth alkali halides, halide salts of zinc and zirconium and halide salts of zirconium oxide or mixtures thereof;
iv) the barbituric acid derivative (a2) is soluble in the monomer (a1) for radical polymerisation;
v) the at least one barbituric acid derivative (a2) is selected from the group consisting of 1-cyclohexyl-5-ethyl-barbituric acid, 1-phenyl-5-ethyl-barbituric acid, and 1,3,5-trimethyl-barbituric acid; and
vi) paste A contains an amount of a polymer (a5) that is soluble in (a1) in a range of 1 to 25% by weight, relative to the total weight of paste A, and paste B contains an amount of a polymer (b5) that is soluble in (b1) in a range of 25 to 85% by weight, relative to the total weight of paste B.

* * * * *